US011464740B2

(12) United States Patent
Weinberger et al.

(10) Patent No.: US 11,464,740 B2
(45) Date of Patent: Oct. 11, 2022

(54) METHOD AND DEVICES FOR DELIVERING THERAPEUTICS BY ORAL, RESPIRATORY, MUCOSAL, TRANSDERMAL ROUTES

(71) Applicants: Board of Supervisors of Louisiana State University and Agricultural and Mechanical College, Baton Rouge, LA (US); MUSC FOUNDATION FOR RESEARCH DEVELOPMENT, Charleston, SC (US); APPLIED RESEARCH CENTER, Aiken, SC (US)

(72) Inventors: Paul M. Weinberger, Bossier City, LA (US); George Wicks, Aiken, SC (US); William D. Hill, Johns Island, SC (US)

(73) Assignees: BOARD OF SUPERVISORS OF LOUISIANA STATE UNIVERSITY AND AGRICULTURAL AND MECHANICAL COLLEGE, Baton Rouge, LA (US); MUSC FOUNDATION FOR RESEARCH DEVELOPMENT, Charleston, SC (US); APPLIED RESEARCH CENTER, INC., Aiken, SC (US)

( * ) Notice: Subject to any disclaimer, the term of this patent is extended or adjusted under 35 U.S.C. 154(b) by 212 days.

(21) Appl. No.: 16/862,540

(22) Filed: Apr. 29, 2020

(65) Prior Publication Data

US 2020/0360288 A1 Nov. 19, 2020

Related U.S. Application Data

(60) Provisional application No. 62/840,326, filed on Apr. 29, 2019.

(51) Int. Cl.
*A61K 9/50* (2006.01)
*A61K 9/16* (2006.01)

(52) U.S. Cl.
CPC .......... *A61K 9/1611* (2013.01); *A61K 9/1694* (2013.01)

(58) Field of Classification Search
None
See application file for complete search history.

(56) References Cited

U.S. PATENT DOCUMENTS

| 4,103,002 | A | 7/1978 | Hench et al. |
| 4,159,358 | A | 6/1979 | Hench et al. |
| 4,171,544 | A | 10/1979 | Hench et al. |
| 4,189,325 | A | 2/1980 | Barrett et al. |
| 4,234,972 | A | 11/1980 | Hench et al. |
| 4,775,646 | A | 10/1988 | Hench et al. |
| 4,857,046 | A | 8/1989 | Stevens et al. |
| 5,074,916 | A | 12/1991 | Hench et al. |
| 5,204,382 | A | 4/1993 | Wallace et al. |
| 5,840,290 | A | 11/1998 | Hench et al. |
| 6,765,720 | B2 | 7/2004 | Morris et al. |
| 7,329,126 | B2 | 2/2008 | Cook et al. |
| 7,666,807 | B2 | 2/2010 | Heung et al. |
| 8,535,725 | B2 | 9/2013 | Li et al. |
| 10,201,633 | B2 | 2/2019 | Weinberger et al. |
| 2012/0201892 | A1* | 8/2012 | Li ........................ A61K 9/501 424/490 |
| 2012/0276164 | A1 | 11/2012 | Tuominen et al. |
| 2017/0354755 | A1* | 12/2017 | Weinberger ............ A61L 27/52 |

FOREIGN PATENT DOCUMENTS

| CA | 2768242 C | 11/2015 |
| EP | 0859813 B1 | 8/1998 |
| WO | 9117777 A3 | 11/1991 |
| WO | 9844965 A1 | 10/1998 |
| WO | 00/30561 A1 | 6/2000 |

OTHER PUBLICATIONS

Li et al. Nanomedicine, Nanotechnology, Biology and Medicine 6 (2010): 127-36 [To Follow].
Baino (Materials Letters 212 (2018) 12-15 [To Follow].
Fu et al. describe the use of hollow calcium hydroxyapatite microspheres for the controlled delivery of proteins. (J Mater Sei Mater Med. Mar. 2011; 22(3): 579-591 [To Follow].

* cited by examiner

*Primary Examiner* — Susan T Tran
(74) *Attorney, Agent, or Firm* — Carin R. Miller, Esq.; Johnson, Marcou, Isaacs & Nix, LLC

(57) ABSTRACT

Methods and monodisperse glass microsphere composites comprising a porous wall hollow-glass microsphere; a cargo of a therapeutic is loaded inside of the porous wall hollow-glass microsphere; and a first shell fully encapsulating the porous wall hollow-glass microsphere and capping pores in the walls, retaining the cargo inside of the porous wall hollow-glass microsphere.

10 Claims, 3 Drawing Sheets

METHOD AND DEVICES FOR DELIVERING THERAPEUTICS BY ORAL, RESPIRATORY, MUCOSAL, TRANSDERMAL ROUTES

CROSS REFERENCE TO RELATED APPLICATIONS/PRIORITY

The present invention claims priority to U.S. Provisional Patent Application No. 62/840,326 filed Apr. 29, 2019, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

BACKGROUND

Glass Microsphere Composites (GMCs) are a recently developed composite material, comprising glass microspheres of one or more compositions (solid, hollow, and porous wall hollow) combined with a biocompatible matrix that coats and interacts with the spheres to form a composite material. This material has properties different from either of the individual components separately, much in the way fiberglass differs from epoxy glue and E-glass fibers.

Use of GMCs often requires use of GMCs where the glass microsphere component is specifically porous wall hollow-glass microspheres (PWHGMs). Furthermore, there are two existing methods where the PWHGM component can be used as a drug delivery platform. In the first, as taught by Li et al, individual PWHGMs are manufactured, and the drug is sequestered inside the microsphere by sealing the PWHGM shell nanopores. These nanopores exist within the wall or shell of the PWHGM, and sealing enables delivery of drug over hours. Such method is unsuitable for delivery of drug over days to weeks, or within a harsh environment such as the stomach where the pore-sealing agent would be rapidly degraded (thus releasing the cargo too soon).

The second method, as taught by Weinberger el al (2019), is creating a composite material sealing a drug within the microspheres by surrounding or coaling them in a hydrogel matrix. In this second scenario, the microspheres are present as an aggregate within the hydrogel matrix. It is unsuitable for use within the GI system or in the blood, because the matrix surrounding the microspheres would be rapidly diluted and washed away.

There are issues with the current technology. One version only allows for the sealing agent to be present within the nanopores, and enables release on the order of hours (up to 4 as disclosed) but not days or weeks. Furthermore, the dextran agent disclosed by the one version would be rapidly degraded in the stomach yielding release time of even less than 4 hours. The composite taught by a second version of current technology is also unsuited for solving present problems, as the biocompatible matrix would be washed away quickly in the stomach thus exposing the microsphere content to rapid release.

There does not exist an obvious means to enable intravenous or gastrointestinal delivery of GMCs or PWHGMs to deliver drug cargo over weeks to months.

SUMMARY

Wherefore, it is an object an embodiment of the present invention to overcome the above-mentioned shortcomings and drawbacks associated with the current technology.

The present invention relates to methods and monodisperse glass microsphere composites comprising a porous wall hollow-glass microsphere; a cargo of a therapeutic is loaded inside of the porous wall hollow-glass microsphere; and a first shell fully encapsulating the porous wall hollow-glass microsphere and capping pores in the walls, retaining the cargo inside of the porous wall hollow-glass microsphere. According to a further embodiment the first shell includes hydrogel. According to a further embodiment each porous wall hollow-glass microsphere is individually surrounded with hydrogel, separate from any adjacent porous wall hollow-glass microsphere. According to a further embodiment the first shell is cured with one of UV light, a reaction with an acid or base, heat, or a chemical agent in a carrier fluid. According to a further embodiment the monodisperse glass microsphere composite of further comprises a second shell encompassing and enclosing the first shell. According to a further embodiment a material comprising the first shell is distinct from a material comprising the second shell. According to a further embodiment the cargo is one of low water solubility and bitter in taste. According to a further embodiment the monodisperse glass microsphere composite further comprises a ferromagnetic material in one of the first shell and the porous wall hollow-glass microsphere. According to a further embodiment ferromagnetic material is one of iron, iron alloy, cobalt steel, and hard- or soft-ferrites.

The present invention further relates to devices and methods of treating a disease in a patient comprising administering a pharmacologically effective dose of a therapeutic encapsulated in a plurality of monodisperse glass microsphere composites, wherein the monodisperse glass microsphere composite comprises a porous wall hollow-glass microsphere; a cargo of the therapeutic is loaded inside of the porous wall hollow-glass microsphere; and a first shell encapsulating the porous wall hollow-glass microsphere and capping porous walls, retaining the cargo inside of the porous wall hollow-glass microsphere. According to a further embodiment the disease is malaria and the therapeutic is one or more of monoterpines, diterpines, triterpines, sesterterpines, sesquiterpenes, sesquiterpenoids, polyterpenes, and norisoprenoids. According to a further embodiment the therapeutic is a sesquiterpenoid, a non-sesquiterpenoid, and both a sesquiterpenoid and a non-sesquiterpenoid, and the sesquiterpenoid is one or more of artemensinin, artemether, artensuate, and dihydroartemensinin and the non-sesquiterpenoid is one or more of lumefantrine, mefloquine, amodiaquine, sulfadoxine, pyrimethamine, piperaquine, chlorproguanil, and dapsone. According to a further embodiment the disease is sickle cell and the cargo is Hydroxyurea. According to a further embodiment the cargo is hydrophobic. According to a further embodiment the monodisperse glass microsphere composites are administered to the patient via IV. According to a further embodiment the monodisperse glass microsphere composites are administered to the patient via aqueous suspension. According to a further embodiment the monodisperse glass microsphere composites are administered to the patient via one of oral, respiratory, mucosal, transdermal route.

The present invention further comprises devices and methods of fabricating a plurality of monodisperse glass microsphere composites comprising filling a plurality of porous wall hallow-glass microspheres with a load; dispersing each of the loaded porous wall hallow-glass microspheres through an inner passage into a flow of a shell fluid; and curing the shell fluid into a shell with one of UV light, a reaction with an acid or base, heat, or a chemical agent in a carrier fluid; wherein the inner passage having a passage width of between 1.0 times a diameter of the loaded porous wall hallow-glass microspheres and 1.9 times a diameter of the loaded porous wall hallow-glass microspheres, and the shell fluid is within the flow of a carrier fluid. According to a further embodiment the method further comprises forming single-microsphere emulsion droplets in the carrier fluid, wherein the carrier fluid that is not miscible with the shell fluid. According to a further embodiment the inner passage is one of an inner cylinder of a three concentric cylinders and located in a microfluidic chip.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

In FIG. 1A, a first method is shown where the active pharmaceutical ingredient (API) can be retained within the internal hollow volume by a sealing agent (e.g. dextran) within the nanopores. In FIG. 1B, a second method is shown where the API within the PWHGM internal hollow volume can be retained by surrounding and coating the PWHGMS with a biocompatible matrix. In such morphology of Glass Microsphere Composite (GMC), the microspheres exist en-mass within a body of matrix. The matrix can be disrupted in an aqueous environment such as the gastrointestinal tract, causing premature release of drug. In FIG. 1C, one embodiment of the presently disclosed invention, a unique morphology of GMC, is shown, comprising a plurality of single microspheres, each surrounded by individual coating layer or layers. Each GMC particle is separate from other GMC particles, making this morphology uniquely suited to use in the gastrointestinal tract as well as other uses.

DETAILED DESCRIPTION

Figure 1A:
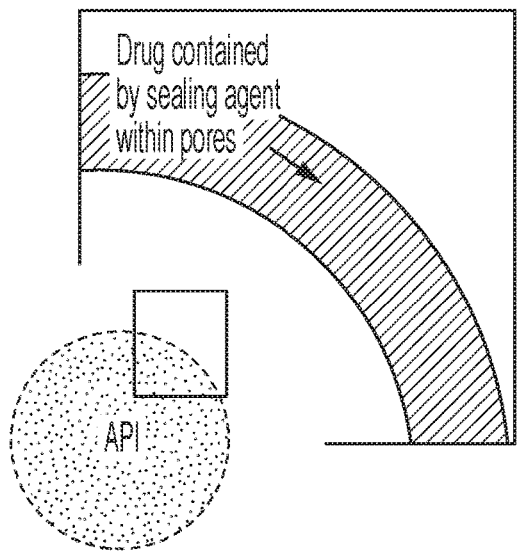
FIGS. 1A-1C show methods for using PWHGMs as a drug delivery platform.
Figure 1B:
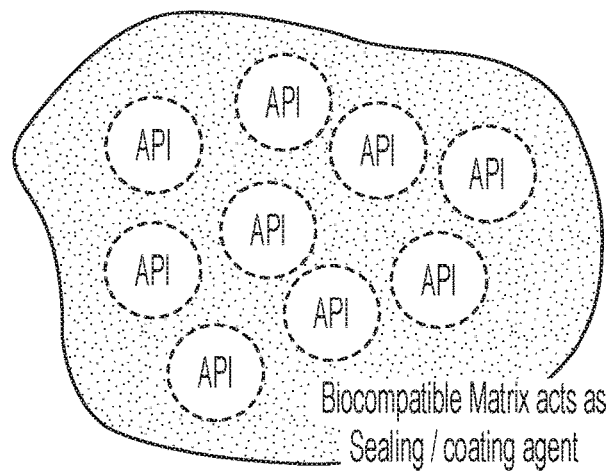

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

The term "glass microspheres" refers to spheres of glass having a diameter of less than 1 mm and includes solid glass microspheres, hollow glass microspheres and/or porous wall hollow glass microspheres, all with smooth surfaces to facilitate packing and delivery, and minimize immunologic response Preferred diameters are 10 to 100 µm, a more preferable diameter 20-60 µm. In a preferred embodiment, the glass microspheres used in the disclosed invention are substantially the same size, having a mean diameter. In an embodiment, a range of widths between 105% of the diameter of the mean diameter and 95% of the diameter of the mean diameter on the small side encompasses the diameter of one of more than 80%, more than 90%, more than 95%, and at least 99.9% of diameter of the glass microspheres used.

The term "composite" includes a combination of glass microspheres and coatings optimized for the applications desired. This combination results in unique properties of the composite compared to the properties of each of the individual components alone.

The term "biological molecule" refers to any carbohydrate, lipid, protein, ribonucleic acid, deoxyribonucleic acid, antibody or fragment thereof, proteoglycans, glycoproteins, or combination of these.

The term "soft tissue", as used herein, refers to tissues that connect, support, or surround other structures and organs of the body. Soft tissue includes muscles, fibrous tissues and fat.

The term "subject or patient" refers to a mammal, primate and preferably a human.

The terms "subepidermal administration" or "subcuticular administration", as used herein, refer to administration beneath the epidermis of the skin, including administration into the dermis, subcutis or deeper, such as submuscularly, or into the periosteum where applicable (in the vicinity of bone tissue.

Glass Microsphere Composites. The disclosed therapeutic delivery system contains a plurality of porous wall hollow glass microspheres, each individually loaded with a therapeutic and incased in a casing. One embodiment provides glass microspheres having a diameter of less than 1 mm and greater than 1 µm. In some embodiments, the glass microspheres have a diameter ranging from about 2 µm to about 500 µm or 2 to 300 µm or 10 to 100 µm. Preferred diameters are 10 to 50 µm, or 10 to 60 µm, and more preferred diameters are 5 to 20 µm, 20 to 40 µm, 20 to 60 µm, or 40 to 60 µm. In one embodiment the composite is implanted by injection. In a further embodiment the injection is performed through a needle with a diameter ranging from about 30 to about 18 gauge. In a further embodiment the injection is performed through a 21, 23, or 25-gauge needle.

The glass microspheres can be all the same diameter or can have multiple diameters in the described ranges. In certain embodiments, the microspheres are all one type, and in other embodiments, multiple types of microspheres are combined.

In certain embodiments, the glass microspheres are coated. The glass microspheres can be coated with a chemical, element, drug, biological molecule, polymer or a combination thereof. The coating can contain or be attached to, a moiety allowing targeting of the glass microspheres to a specific organ, tissue or cell type.

Porous wall hollow glass microspheres (PWHGM) can be loaded with cargo including but not limited to biological molecules, chemicals, elements, or other materials. In one embodiment the cargo can be a pigment or coloring agent. The PWHGM can be loaded with one or more therapeutic agents such as antibiotics, anti-inflammatory agents, growth factors, cytokines, chemokines, chemotherapeutic agents, cytotoxic agents, antibodies, or combinations thereof. The PWHGM can be loaded with cargo of living biological elements such as cells, bacteria, viruses, or combinations thereof. The cargos above can exist alone or in various combinations. The loaded PWHGM can be modified to delay or extend the release of cargo from the PWHGM once the PWHGM have been administered to a subject.

Density, sizes and size distributions of microspheres, viscosities of solutions, can be modulated for desired uses.

Solid Glass Microspheres. Commercially Available Solid Glass Microspheres. Some embodiments include solid glass microspheres, alone or in combination with other microspheres. The methods for the manufacture of solid glass microspheres is well known to those skilled in the art, and solid glass microspheres are commercially available for example from a variety of sources including, but not limited to Potters Industries LLC, CoSpheric Innovations and Microtechnology, and MoSci Corp., and Polysciences, Inc. Exemplary solid glass microspheres are made of borosilicate or soda-lime. The microspheres are typically sieved to specific diameter ranges, and they are provided in powder form.

Methods of Making. A number of processes have been devised for the production of spherical glass bodies in small sizes. These generally involve the free suspension of particles in a hot zone for a time and at a temperature sufficient to permit each particle to be drawn into a spherical shape by surface tension. For economical commercial production of glass microspheres, it is important that the viscosity of the glass generally be relatively low at a reasonable melting temperature (for example, no greater than about 1350° C.). Generally, additions of alkali and fluorine are used to reduce viscosity and melting temperature; however, the use of fluorine creates an environmental concern as it is readily lost during the melting process and the addition of alkali typically results in microspheres that are of lower chemical durability and that are hydrophobic and tend to clump and be poorly flowing (See U.S. Pat. No. 6,765,720). However, other agents can also be added to increase or improve the 'flowability' of the microspheres.

Bio-active particulate glass may be prepared according to the methods of the art such as taught in U.S. Pat. Nos. 4,159,358; 4,234,972; 4,103,002; 4,189,325; 54,171,544; 4,775,646; 4,857,046, 5,074,916 and 5,840,290. For example, the raw materials (e.g., $SiO_2$, CaO, $Na_2O$ and $P_2O_5$) are mixed in Nalgene® plastic container on a ball mill for four hours. The mix is then melted in a platinum crucible at 1350° C. and homogenized for 24 hours. The molten glass is poured into distilled, deionized water to produce a glass frit. The frit is ground in a mortar and pestle and passed through ASTM sieves to produce the required particle size range.

Hollow Glass Microspheres. Commercially Available Hollow Glass Microspheres. Several embodiments provide composites containing hollow glass microspheres. The manufacture of hollow glass microspheres is well known by those skilled in the art, and hollow glass microspheres are commercially available for example from 3M (St. Paul, Minn.), Bariteworld (Rockleigh, N.J.) and other sources.

Methods of Making Hollow Glass Microspheres. Hollow glass microspheres can be produced by a variety of techniques. In one approach, glass powder along with a blowing agent is fed into a hot zone in a furnace, which softens the glass to allow formation of spherical particles. The blowing agent becomes unstable as it is heated, producing a glass bubble that expands to produce hollow glass microspheres. The material is quenched, and a flotation process is used to retrieve the desired initial products.

Porous-Wall Hollow Glass Microspheres. Suitable porous wall hollow glass microspheres can be produced according to the methods taught in U.S. Pat. Nos. 7,666,807 and 8,535,725 both of which are incorporated by reference in their entireties. These porous wall hollow glass microspheres can be obtained from commercial sources such as MoSci Corp (Rolla, Mo.). Briefly, feed for producing porous wall hollow glass microspheres is a 20- to 40-µm sodium borosilicate glass powder, and containing a sulfate blowing agent. The powder is fed into a hot zone produced by a controlled gas-air flame, which softens the glass to allow formation of spherical particles. The blowing agent becomes unstable as it is heated, producing a glass bubble that expands to produce hollow glass microspheres. The material is quenched, and a flotation process is used to retrieve the desired initial products. The hollow glass microspheres are then converted into porous wall hollow glass microspheres by heat treating to produce two glass phases in the thin outer walls, one rich in silica and the other in sodium and boron They are then leached in hydrochloric acid, which preferentially leaches the sodium- and boron-rich phase, leaving behind interconnected channels in the silica-rich phase and through wall porosity. Dry sieving can then be performed to produce uniform and specific sizes or alternatively, produce wider size distributions as desired.

An exemplary hollow glass microsphere has a porous wall surrounding an internal volume. The porous wall can have a unique pore morphology and diameter of about 1 nanometer (nm) to about 100 nm. In some embodiments, the porous wall has a pore diameter of about 10 nanometers (nm).

The pores within the walls of the porous wall hollow glass microspheres can be gated with a gating agent. In one embodiment the gating agent is a sol-gel glass. In another embodiment, the gating agent is a dopant added to the base glass composition. In still another embodiment, the gating agent is a polymer, biological molecules, colloidal starch, polymerized fibrin, or chemical.

The outer surface of the various types of microspheres can be coated to enhance properties and uses, and are further described below. In one embodiment, the microspheres are coated with a compound, biological molecule, or polymer. In one preferred embodiment the coating is polyvinylpyrrolidone.

To emphasize, a unique feature of the Porous Wall Hollow Glass Microspheres is that a through-wall, interconnected porosity can be created and controlled through the thin outer shells, due to the glass composition and heat-treatments used, which can produce phase separation and two different glass phases in the outer shells. One of these phases is an interconnected worm-like structure of a relatively soluble composition that when leached, can produce a very unique through-wall porosity that can be controlled on a scale of about 1 to 100 nm. The porosity allows filling of the microspheres with a variety of cargos (liquids, gases or solids) for a variety of potential applications.

The present invention is directed towards a new drug delivery device, particularly suited to delivery of medications by oral, topical, intravenous, and inhalation routes as well as implantation or intramuscular injection. While there are many existing methods of encapsulating and releasing compounds for the purposes of drug delivery, there remain several challenges and problems that existing technology does not address. One is the delivery of protein- or peptide-based medications via oral administration. These are rapidly degraded in the stomach and/or small intestine. Another challenge is the creation of oral liquid formulations of medications. Liquid formulation is desirable for medications that will be used to treat pediatric patients, because the dose is easily titratable to the patient's body mass. Many pediatric patients are unable to safely swallow pills or tablets. Barriers to developing liquid formulations include: unpleasant taste (common to most medications); poorly water-soluble compounds pose significant challenge; highly water-soluble drugs are very difficult to create extended release versions; many drugs are subject to alteration or degradation in the stomach. The present invention leverages a recently developed class of materials, Glass Microsphere Composites (GMCs), and teaches a novel form of these composites, monodispersed single-microsphere composites. This morphology has never been described before and is entirely novel.

Figure 1C:
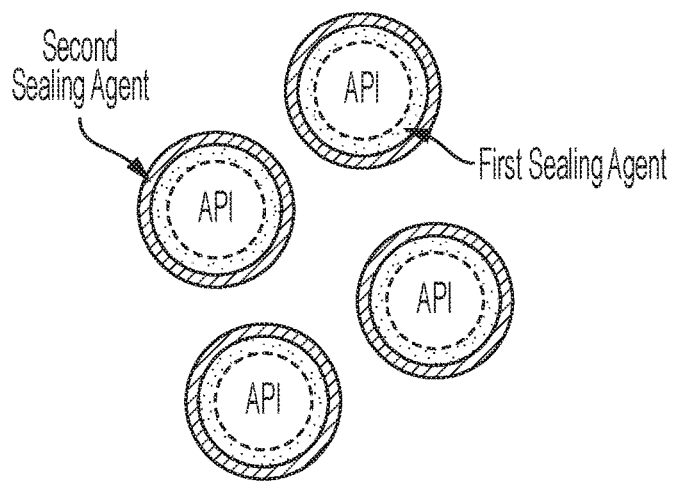

Here, the inventors teach a new material (monodisperse glass microsphere composites) including a method to surround each microsphere individually (rather than as an aggregate) with hydrogel to form a novel material comprised of single-sphere composites (see FIG. 1C), and the uses of this new material.

The disclosed invention overcomes the obstacles described above with current technology and will allow use of the monodisperse glass microsphere composites to delivery gas, liquid, or solid drugs over days to weeks, or within a harsh environment such as the stomach. Additionally, this new material will be efficacious for deep implantation (e.g. intramuscular or other), topical use, or inhalation uses. The material can be targeted for specific areas, such as the ilium, jejunum, or even large intestine by embedding targeting agents in the coating layer or attaching them as a third layer.

These monodisperse glass microsphere composites are ideal for use in various biomedical applications, including as an injectable tissue filler for surgical applications, or as a drug delivery device for liquid, solid, or gas compounds.

Figure 2A:
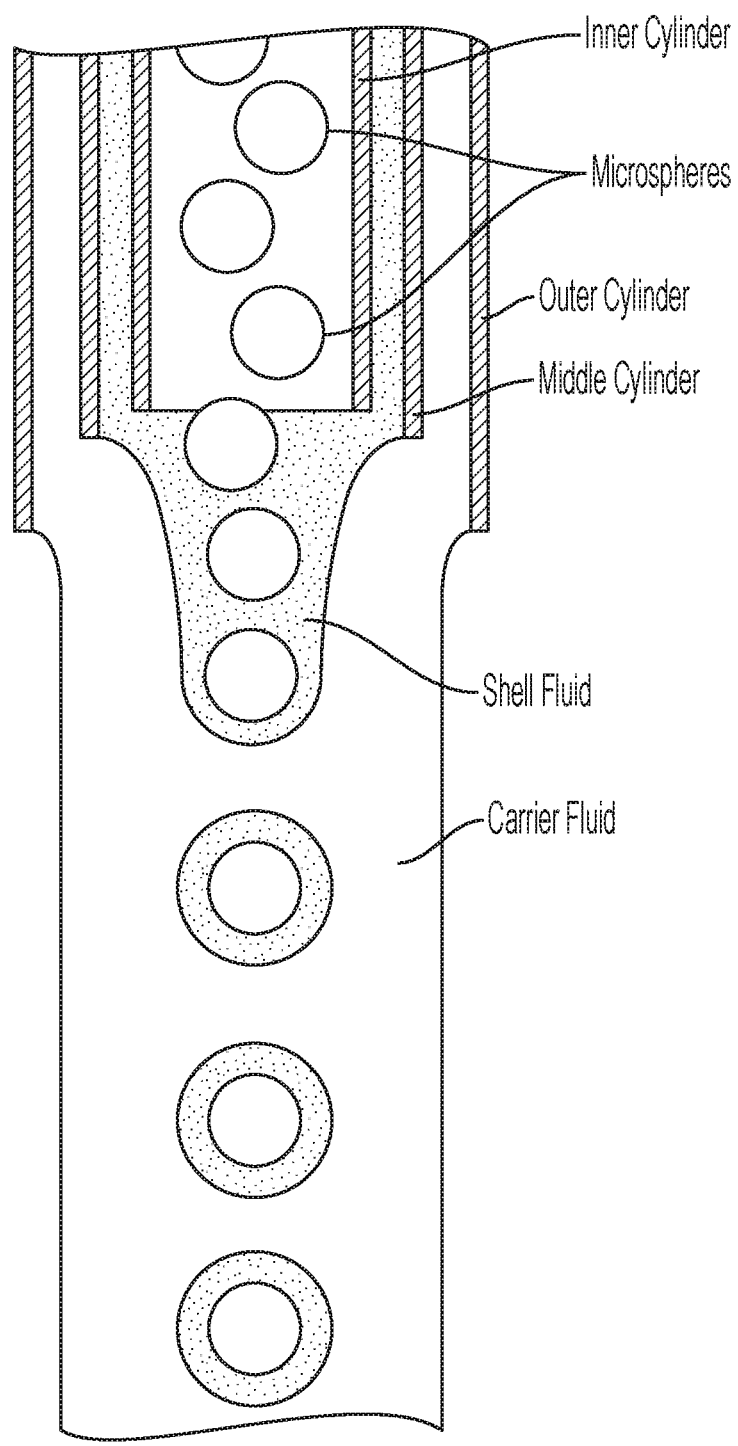
FIGS. 2A and 2B are schematic illustrations of two embodiments of methods to fabricate the monodisperse glass microsphere composite depicted in FIG. 1C.
Figure 2B:
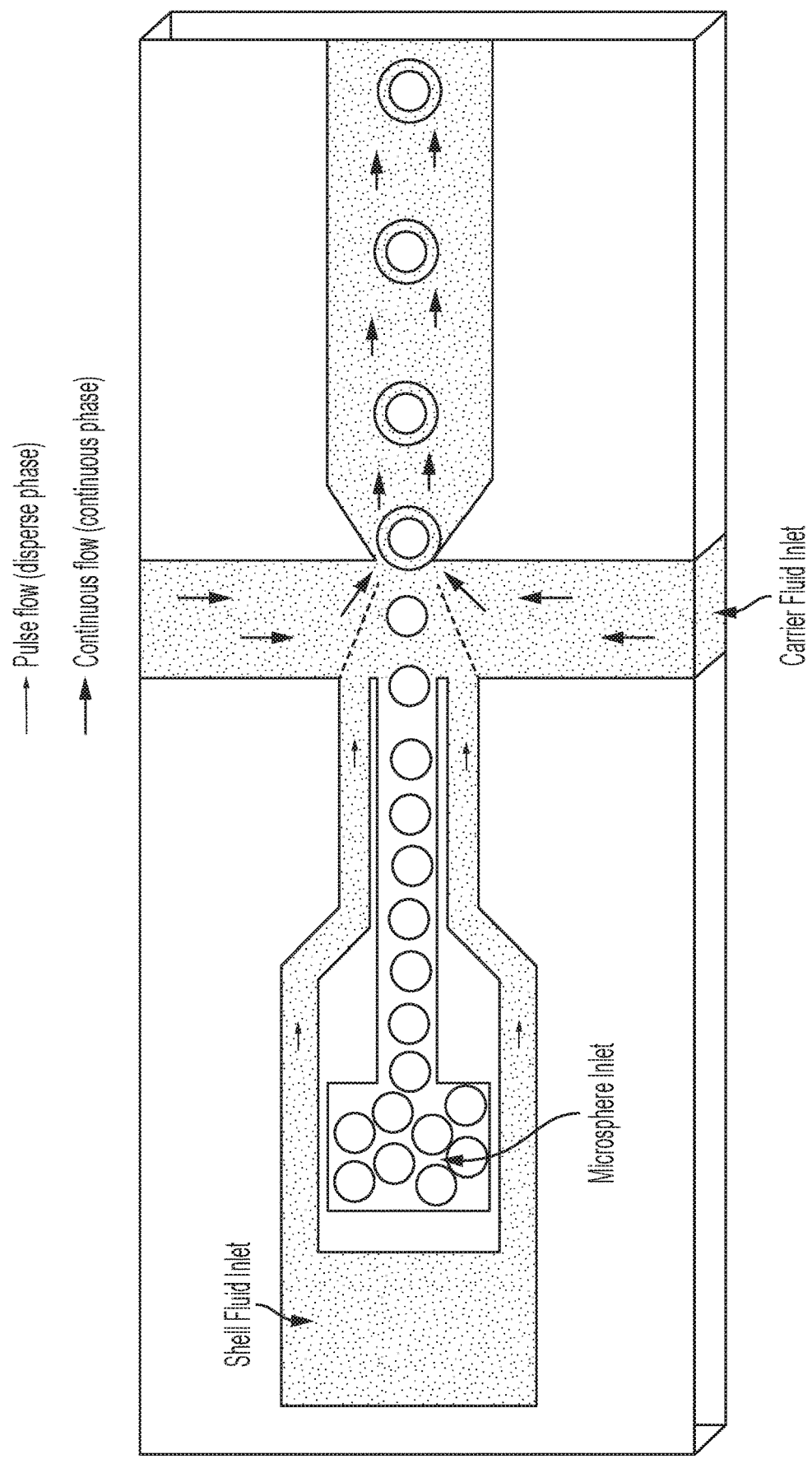

Turning to FIGS. 2A and 2B, methods of producing monodisperse glass microsphere composites is shown. Single-droplet composite material is prepared via microfluidics device, where the internal sheathe is slightly larger than the microsphere diameter. This forces the microspheres to be dispensed single-file. They are dispensed into a channel of shell fluid (e,g, hydrogel or coating agent) delivered by larger diameter channel, and finally into a carrier fluid that is not miscible with the shell fluid. This forms single-drop suspensions each containing a single PWHGM, with in cargo intact, surrounded by a hydrogel/coating agent. The shell can be cured (e.g. by UV light, reaction with acid or base, heat, or a chemical agent in the carrier fluid). In a further embodiment, a second shell may additionally be added by having a the first shelled monodisperse glass microsphere composites dispensed into a second into a channel of second shell fluid, which can then be delivered into a carrier fluid.

An alternative method utilizes a microfluidic chip to produce single-droplet emulsions where the internal phase of the emulsion consists of a single microsphere plus liquid phase. This liquid phase contains the medication or therapeutic, and is present inside and outside the microspheres owing to their unique through-wall porosity. Several microdfluidic methods are known to those skilled in the art for producing single- and even double-emulsions. In the example depicted, the microspheres are in a central channel, with the shell fluid adjacent. These are dispensed in a pulsatile fashion into a continuously flowing carrier fluid that is not miscible with the shell fluid. The microspheres become surrounded by shell fluid, and then form single-microsphere emulsion droplets in the carrier fluid.

One specific application of the present invention is in the treatment of sickle cell disease. A pressing unmet public health need of children is the development of age-appropriate oral drug formulations. Of the 160 essential medicines identified by the World Health Organization (WHO), only 47 are available in pediatric oral formulations. One such drug is Hydroxyurea (HU), originally developed as a chemotherapeutic agent but now an important treatment for sickle cell disease. HU works by inducing a shift from adult to fetal hemoglobin transcription and thereby decreasing the severity of the disease. It is now recommended as first line therapy for all SSD patients beginning at 9 months of age. This is problematic, as HU is only available as a tablet or capsule. Administration to children under one year old therefore requires the drug to be compounded into a liquid by individual pharmacies and hospitals. This practice is concerning because it introduces opportunity for variable bioequivalence and safety. By filling the internal hollow volume of the PWHGMs with HU, and then individually sealing them to produce single-microsphere GMCs, the resulting particles have no taste and can be easily placed into suspension in a pleasant tasting syrup. The resulting liquid medication is suitable for oral administration to children, and allows easy weight-based dosing by measuring the appropriate volume of liquid suspension.

A second specific application of the present invention is in the treatment of malaria. While much progress has been made in devising new treatments for this disease, there remains an enormous amount of human suffering and death from this disease. One of the most difficult problems relates to difficulty delivering effective medications to patients with active malaria. Up to 70% of plasmodium in many endemic areas are now resistant to chloroquine. Therefore, the currently recommended therapies consist of an artemensinin derivative combined with another antimalarial compound (e.g. artesunate/mefloquine, or artemether/lumefantrine). As used here and throughout, the term artemensinin refers to not only the sesquiterpenoid artemensinin, but also natural and artificially derived compounds functionally related to artemensinin. Such artemensinins are almost universally rapidly degraded with half-lives generally in the two- to four-hour range. Thus, patients must take multiple pills over several days, and treatment failures can approach 30% in some cases. An additional problem relates to parenteral administration of artemensinin derivatives, vital in cases of severe life-threatening malaria. IV formulations are relatively expensive and not practical for the areas of the world where such therapy is needed most. The less expensive artemensinins are very poorly water soluble (0.06 to 0.45 mg/ml), and thus must be delivered as intramuscular injection of the artemensinin-derivative in an oil-based excipient. Such injections, because of the oil phase, are very painful. By sequestering the anti-malaria medications inside of the protective glass cocoon of the monodisperse glass microsphere composites, the limitations with the current technology are abrogated and the drugs can be delivered either orally or as intramuscular injection. When used for oral delivery, the monodisperse glass microsphere composites allow for extended release of the artemensinin over hours to days. This allows for fewer pills, potentially even a single dose. Additionally, artemensinin delivery using this approach would produce a more steady-state dose compared to the rapid rise and fall of current oral therapies. This is important because treatment must account for the plasmodium organism's 48-hour life cycle in humans—drug sensitivity peaks and wanes over this time, thus requiring prolonged treatment. When used for intramuscular injection, the artemensinin is again sequestered within the protective glass cocoon of the monodisperse glass microsphere composites, sealed with a hydrophobic sealant and can thus be suspended in normal saline for the injection. The monodisperse glass microsphere composites are small enough, even when surrounded by a coating layer, to easily be injected through needles commonly used for intramuscular injection.

In one particular embodiment, monodisperse glass microsphere composites are used to allow delivery of medications effective for the treatment of malaria. In a preferred embodiment, the medications consist of one or more compounds from the group consisting of monoterpines, diterpines, triterpines, sesterterpines, sesquiterpenes, sesquiterpenoids, polyterpenes, and norisoprenoids. In a more preferred embodiment, the compound is one or more sesquiterpenoids, selected from the group consisting of artemensinin, artemether, artensuate, and dihydroartemensinin. In yet another preferred embodiment, the medications contain one or more compounds from the group consisting of lumefantrine, mefloquine, amodiaquine, sulfadoxine, pyrimethamine, piperaquine, chlorproguanil, and dapsone. In a more preferred embodiment, the medications consist of a combination of one or more of these compounds together with one or more sesquiterpenoids.

In some embodiments of the invention, the monodisperse glass microsphere composites loaded with one or more drugs are individually surrounded by a coating layer, sealing the drug within the internal payload. In a preferred embodiment the coating layer is applied using microfluidics to create single droplet emulsions around each microsphere.

Ferromagnetic material can be incorporated into the monodisperse glass microsphere composites to allow them to be easily manipulated, or even removed from the body. In some embodiments of the invention, the monodisperse glass microsphere composites are loaded with a ferromagnetic compound. In a preferred embodiment, the ferromagnetic compound is selected from the group consisting of iron, iron alloys, cobalt steel, and hard- or soft-ferrites.

The monodisperse glass microsphere composites will allow packaging, delivery, and release of therapeutic compounds comprising gasses, liquids, and/or solids or combinations thereof. These compounds can be volatile, reactive, subject to rapid degradation or spoilage, and can be sequestered inside the microscopic glass "cocoons" thereby allowing use of compounds not possible before the disclosed monodisperse glass microsphere composites. With the monodisperse glass microsphere composites, the release of the compound(s) can be controlled, to occur from hours to days, to months. Release can also be initiated as desired, for instance through light (photoactivated release), or highly focused ultrasound. The delivery routes enabled by the monodisperse glass microsphere composites packaging and controlled release are applicable to oral, intravenous, intramuscular, topical, and inhalation routes.

For oral medication in particular, the monodisperse glass microsphere composites will allow packaging and delivery of medications in a liquid suspension for pediatric drug delivery. The ability to package poorly water soluble and bitter compounds is particularly important, as these are currently very difficult to create oral liquid formulations for pediatric use. Another distinct and highly competitive advantage of the monodisperse glass microsphere composites vis-a-vis oral medication, is the ability to sequester and deliver drugs and compounds that are volatile or labile, or subject to rapid degradation. For instance, peptide-based therapeutics are difficult to administer orally because they are rapidly cleaved by acid hydrolysis and pepsin in the stomach. These could be sequestered in the monodisperse glass microsphere composites until reaching a specific environment, for instance the ilium or even large intestine. Release could be titrated and controlled over hours or days. Release is even possible over weeks if the spheres are also targeted for persorption or adherence to the intestinal epithelium, or attached to a means of physically retaining them within the stomach or small intestine.

There are a variety of commercial products and applications that could utilize the monodisperse glass microsphere composites, such as bandages/wound dressings for antibiotic and/or pain-control medication delivery; delivery of topical blood clotting agents for battlefield/trauma dressings; delivery of oral formulation of medications, especially ones with challenging oral delivery issues (poor water solubility, bitter taste, degraded in stomach, need for sustained delivery); delivery of topical medication over long-term sustained release (days to weeks); delivery of medication via micro-injection, especially for long-term sustained release; and delivery of medication by inhalation, especially for sustained-release.

The monodisperse glass microsphere composites provide several key advantages for the delivery of medication via multiple routes (topical, oral, inhalation). For all three routes, the monodisperse glass microsphere composites will allow packaging, delivery, and release of therapeutic compounds comprising gasses, liquids, and/or solids or combinations thereof. These compounds can be volatile, reactive, subject to rapid degradation or spoilage, and can be sequestered inside the microscopic glass "cocoons" thereby allowing use of compounds not possible before the disclosed monodisperse glass microsphere composites. Release of the compound(s) can be controlled, to occur from hours to days, to months. Release can also be initiated as desired, for instance through light (photoactivated release), or highly focused ultrasound. For oral medication in particular, the monodisperse glass microsphere composites allow packaging and delivery of medications in a liquid suspension for pediatric drug delivery. The ability to package poorly water soluble and bitter compounds is particularly important, as these are currently very difficult to create oral liquid formulations for pediatric use. Another distinct and highly competitive advantage of the monodisperse glass microsphere composites vis-a-vis oral medication, is the ability to sequester and deliver drugs and compounds that are volatile or labile, or subject to rapid degradation. For instance, peptide-based therapeutics are difficult to administer orally because they are rapidly cleaved by acid hydrolysis and pepsin in the stomach. These could be sequestered in the monodisperse glass microsphere composites until reaching a specific environment, for instance the ilium or even large intestine. Release could be titrated and controlled over hours, days, or weeks (if the spheres are also targeted for persorption or adherence to the intestinal epithelium). The monodisperse glass microsphere composites is based on a mature technology, developed for energy/homeland security purposes but not explored for these uses.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

Wherefore, we claim:

1. A method of fabricating a plurality of monodisperse glass microsphere composites comprising:
   filling a plurality of porous wall hollow-glass microspheres with a cargo of a therapeutic load;
   dispersing each of the therapeutic loaded porous wall hollow-glass microspheres through an inner passage into a flow of a first shell fluid;
   forming single-microsphere emulsion droplets in the carrier fluid, wherein the carrier fluid that is not miscible with the shell fluid; and
   curing the shell fluid into a first shell with one of UV light, a reaction with an acid or base, heat, or a chemical agent in a carrier fluid;
   wherein the first shell fully encapsulating the porous wall hollow-glass microsphere and capping pores in the walls, retaining the cargo inside of the porous wall hollow-glass microsphere,
   wherein the inner passage having a passage width of between 1.0 times a diameter of the loaded porous wall hollow-glass microspheres and 1.9 times a diameter of the loaded porous wall hollow-glass microspheres, and the shell fluid is within the flow of a carrier fluid.

2. The monodisperse glass microsphere composite of claim 1, wherein the first shell includes hydrogel.

3. The monodisperse glass microsphere composite of claim 2, wherein each porous wall hollow-glass microsphere is individually surrounded with hydrogel, separate from any adjacent porous wall hollow-glass microsphere.

4. The monodisperse glass microsphere composite of claim 1, wherein the first shell is cured with one of UV light, a reaction with an acid or base, heat, or a chemical agent in a carrier fluid.

5. The monodisperse glass microsphere composite of claim 1, further comprising a second shell encompassing and enclosing the first shell.

6. The monodisperse glass microsphere composite of claim 5, wherein a material comprising the first shell is distinct from a material comprising the second shell.

7. The monodisperse glass microsphere composite of claim 1, wherein the cargo is one of low water solubility and bitter in taste.

8. The monodisperse glass microsphere composite of claim 1, further comprising a ferromagnetic material in one of the first shell and the porous wall hollow-glass microsphere.

9. The monodisperse glass microsphere composite of claim 8, wherein ferromagnetic material is one of iron, iron alloy, cobalt steel, and hard- or soft-ferrites.

10. The method of claim 1, wherein the inner passage is one of an inner cylinder of a three concentric cylinders and located in a microfluidic chip.

* * * * *